(12) United States Patent
Ball et al.

(10) Patent No.: US 8,155,742 B2
(45) Date of Patent: Apr. 10, 2012

(54) REMOTE COMMUNICATION SYSTEM WITH AVAILABILITY INDICATOR FOR AN IMPLANTABLE MEDICAL DEVICE

(75) Inventors: James J. Ball, St. Paul, MN (US); Robert J. Ryan, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1194 days.

(21) Appl. No.: 11/380,139

(22) Filed: Apr. 25, 2006

(65) Prior Publication Data

US 2007/0250130 A1 Oct. 25, 2007

(51) Int. Cl.
*A61N 1/08* (2006.01)

(52) U.S. Cl. .............................. 607/31; 607/60; 607/30

(58) Field of Classification Search ................... 607/60, 607/31, 32
See application file for complete search history.

(56) References Cited

U.S. PATENT DOCUMENTS

| | | | |
|---|---|---|---|
| 5,456,692 A | 10/1995 | Smith et al. | |
| 5,720,770 A * | 2/1998 | Nappholz et al. | 607/30 |
| 6,442,432 B2 * | 8/2002 | Lee | 607/59 |
| 6,727,814 B2 * | 4/2004 | Saltzstein et al. | 340/531 |
| 6,804,558 B2 | 10/2004 | Haller et al. | |
| 6,878,112 B2 | 4/2005 | Linberg et al. | |
| 6,957,107 B2 * | 10/2005 | Rogers et al. | 607/60 |
| 2003/0220673 A1 * | 11/2003 | Snell | 607/60 |
| 2005/0049656 A1 | 3/2005 | Petersen et al. | |
| 2005/0283198 A1 * | 12/2005 | Haubrich et al. | 607/30 |

* cited by examiner

*Primary Examiner* — Carl H Layno
*Assistant Examiner* — Natasha Patel

(57) ABSTRACT

A medical information communication system and corresponding methods are described. The system can permit monitoring the performance of an implantable medical device (IMD) implanted within a body of a patient, monitoring the health of the patient, and/or remotely delivering a therapy to the patient through the IMD. The IMD can be capable of bi-directional communication with a clinician. Further, the system can comprise a communication availability indicator to indicate whether the IMD is available for communication.

22 Claims, 5 Drawing Sheets

| Patient List | | | |
|---|---|---|---|
| Patient ( = Discontinued) | Device | Last Send: ( * =New) | Real-Time Availability Status |
| Jones, Mary PT01211 | Virtuoso DR™ 03-Aug-2004 | | Query |
| Smith, Clyde R. PT04773 | Concerto CRT™ 16-Jul-2004 | 15-Jun-2005* 11:58 AM | Searching... |
| Doeberman, John PT09964 | Virtuoso DR™ 30-May-2005 | 13-Jun-2005* 04:32PM | Found. |
| Miller, Megan PT08225 | Virtuoso DR™ 10-Dec-2004 | 10-Jun-2005 04:32PM | Query |

FIG. 3

REMOTE COMMUNICATION SYSTEM WITH AVAILABILITY INDICATOR FOR AN IMPLANTABLE MEDICAL DEVICE

FIELD OF THE INVENTION

The disclosure relates to implantable medical devices (IMDs).

BACKGROUND OF THE INVENTION

IMDs are capable of communicating with a clinician to transmit data and for programming purposes. Generally, IMDs can communicate with a clinician from a remote site. For example, an IMD may remotely communicate from a patient's home with a clinician. In some instances, the clinician will attempt to initiate communication with the IMD. Unfortunately, the clinician may waste time and resources attempting to communicate with an IMD that is unavailable for communication.

BRIEF DESCRIPTION OF THE DRAWINGS

FIG. 3 shows a web based interface in accordance with an embodiment of the invention;

DETAILED DESCRIPTION OF THE ILLUSTRATED EMBODIMENTS

Figure 1:
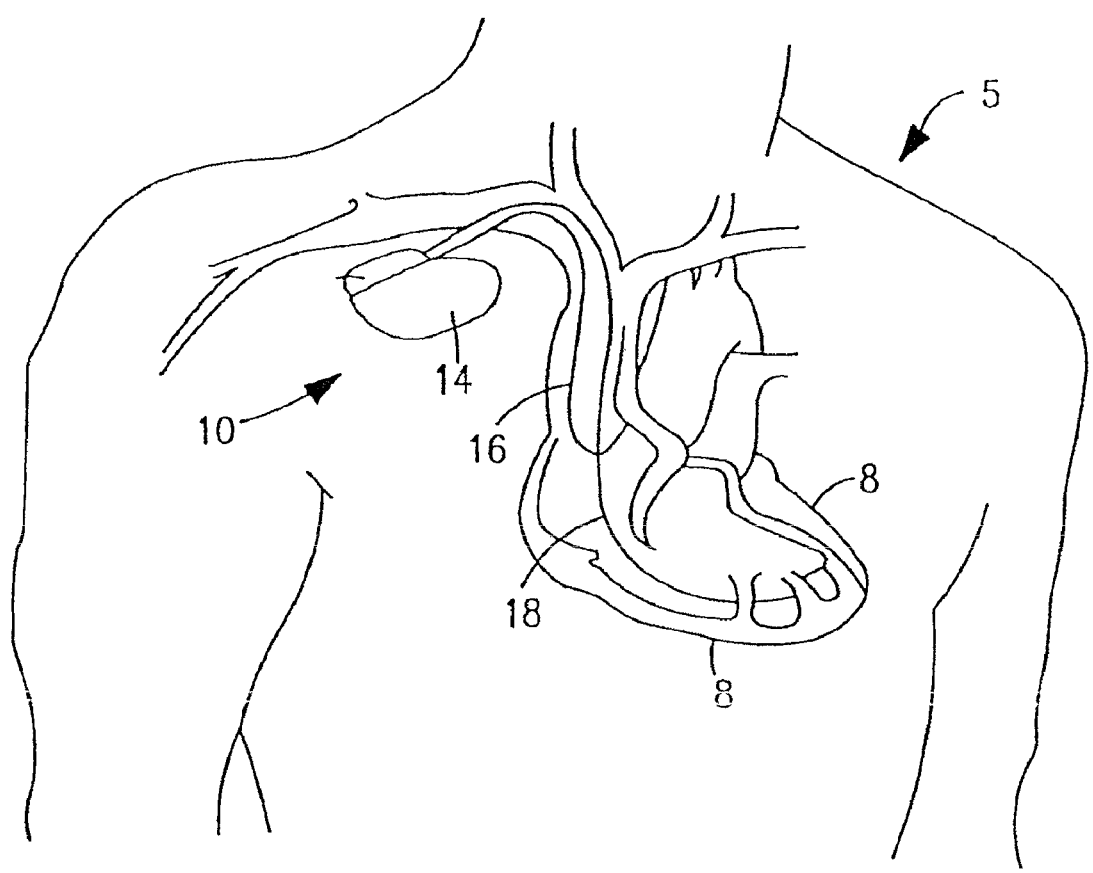
FIG. 1 shows a simplified schematic view of an embodiment of an IMD.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the invention as defined by the appended claims. Thus, the invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives that fall within the scope of the invention.

FIG. 1 is a simplified schematic view of one embodiment of implantable medical device ("IMD") 10 in accordance with an embodiment of the invention implanted in a patient 5. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Although IMD 10 is described as a pacemaker, those of ordinary skill in the art will appreciate that the invention may be advantageously practiced in connection with numerous other types of IMDs, such as implantable cardioverter defibrillators (ICDs), PCD pacemakers/cardioverters/defibrillators, oxygen sensing devices, nerve stimulators, muscle stimulators, drug pumps, implantable monitoring devices, or combinations thereof. Moreover, in some embodiments electrodes on the enclosure 14 may be used in addition to or in substitution for leads 16 and 18.

Figure 2:
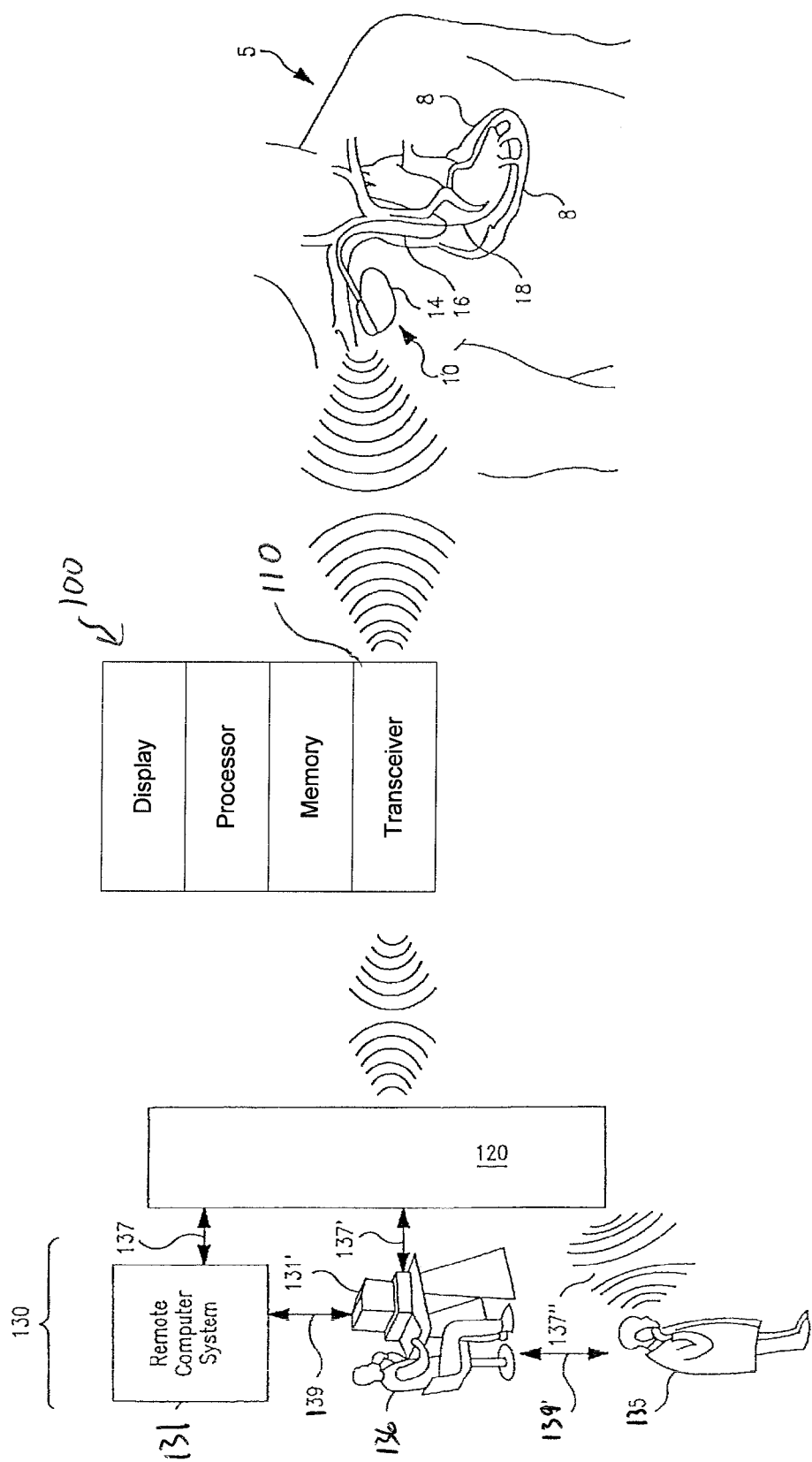
FIG. 2 shows a simplified schematic of various components of a system in accordance with an embodiment of the invention.

In some embodiments, the invention includes a system to provide communication between an IMD and a clinician. Referring now to FIG. 2, there is shown a simplified schematic diagram of representative components of a system in accordance with an embodiment of the invention. In the embodiment of FIG. 2, the system comprises IMD 10, proximate monitor 100, transceiver 110, patient management network 120, and remote system 130. As discussed further below, the system can be adapted to indicate to the clinician whether or not the IMD is available for communication.

The proximate monitor 100 can comprise any device that allows the IMD to communicate with the patient management network. In some embodiments, the proximate monitor 100 can comprise a processor (e.g., microprocessor, CPU, microcomputer or controller) for controlling the operation of module 100 and the exchange of data and information between IMD 10 and transceiver 110, telemetry module for communicating with IMD 10, memory/storage module for storing or recalling information or data in memory, a hard disk, or another computer readable medium such as flash memory, ROM, RAM, EEPROM, and the like, power management module, real time clock for providing timing signals to computing, display and/or user interface. Several of these capabilities are depicted in FIG. 2.

Some embodiments of the proximate monitor 100 include a housing. Transceiver 110 may be contained within the same housing or may be provided with a separate housing. Transceiver and proximate monitor may be connected by any suitable interface, such as via link, connection, cable, line, or wireless link, such as RF or infrared. Transceiver 110 receives information or data from, or sends information or data to, proximate monitor 100. Further, IMD 10 can receive information or data from, or sends information or data to, proximate monitor 100, such as by RF telemetric means. For example, programming commands and/or data be transmitted to IMD 10 by proximate monitor 100, and that information and data can be received by proximate monitor 100 from IMD 10, using RF telemetry protocols such as MEDTRONIC 10, Telemetry A, B or C RF communication standards. Thus, proximate monitor 100 acts as a go-between in respect of the transceiver 110 and IMD 10.

In some embodiments, IMD 10 can monitor various aspects of the patient's health, and store it in memory as information or data. Upon IMD 10 detecting a threshold event (e.g., detection of arrhythmia or fibrillation in patient 5) or receiving instructions from patient 5 or remote system 130, IMD can upload stored information or data to remote system 130 via proximate monitor 100, transceiver 110 and patient management network 120. IMD 10 can be interrogated directly by patient 5, or can be interrogated remotely by remote system 130 via proximate monitor 100 and transceiver 110.

Examples of data or information that can be uplinked to proximate monitor 100 from IMD 10 include, but are in no way limited to, blood pressure data, electrogram data, electrocardiogram data, pH data, oxygen saturation data, oxygen concentration data, QT interval data, activity level data, accelerometer or piezoelectric sensor data, minute ventilation data, transthoracic impedance data, heart rate data, heart rate variability data, ST elevation data, T-wave alternans data, ICD or PCD charging current status, current battery state of charge, drug pump reservoir level status, drug pump reservoir filling status, catheter occlusion data, IMD prescription table, software application versions installed in the IMD, data stored in or acquired by MEDTRONIC CHRONICLE devices, and so on.

Transceiver 110 can include any device useful for communication between the proximate monitor 100 and the patient management network 120. For example, transceiver 110 can include a telephone connected to the patient management network. Of course, as described above, the transceiver 110 could be included with the proximate monitor 100. Further, more than one transceiver can be provided. For example, a first transceiver associated with the proximate monitor can be provided for facilitating communication between the proximate monitor and the IMD. A second transceiver can be provided for facilitating communication between the proximate monitor and the clinician. In some embodiments, transceiver 110 includes a telephone that communicates wirelessly with the patient management network.

Patient management network 120 includes within its scope existing worldwide telephone and Internet communications network. For example, patient management network can include 120 a global system for mobile communications (GSM) network system comprising a mobile station carried by the patient, a base station subsystem for controlling the radio link with the mobile station, and a network subsystem (the main part of which is a mobile services switching center which performs the switching of calls between the mobile and other fixed or mobile network users, as well as management of mobile services, such as authentication), and an operations and maintenance center which oversees the proper operation and setup of the network.

The remote system 130 can comprise any system useful for a clinician to interact with the patient management network. Remote system 130 can comprise or communicate with any one or more of remote computer system 131 or remote computer system 131'. A clinician can include one or more of a remote health care provider, physician, database specialist, clinical specialist, nurse, computer specialist and/or operator 136, and/or remote physician 135. In addition to being capable of communicating with proximate monitor 100 via patient management network 120, remote computer system 131 can communicate directly with computer system 131' and/or clinician through link 139, or through links 137 and 137' via patient management network 120.

Remote computer system 131 can also be configured to communicate directly with a clinician such as physician 135, or to communicate with physician 135 via links 137 and 137" through patient management network 120. Computer system 131' and/or remote health care provider, physician, database specialist, clinical specialist, nurse, computer specialist or operator 136 can also communicate with physician 130 directly through link 139', or through-links 137' and 137" via patient management network 120.

In some embodiments the invention includes a system comprising an IMD in communication with a proximate monitor in communication with a patient management network accessible by a clinician. In such embodiments, the system can be adapted to indicate to the clinician the availability of the medical device to communicate. For example, the system can visually indicate the IMD's availability to the clinician via a web based user interface.

An example of a user interface having an availability indicator is shown in FIG. 3. Column C1 identifies the patient by name and patient number. Of course, any other suitable information could be used to identify the patient. Optionally, the interface could also show the type of IMD associated with the patient, as shown in column C2. Other optional information the interface could display includes the time and/or date the IMD last communicated with or was last available for communication, as shown in column C3. Columns C4 and C5 show an embodiment of an availability indicator. In this example, column C4 shows the availability of the IMD in real time and column C5 shows the status of the IMD.

In the example of FIG. 3 there are four patients displayed on the user interface, indicated as patients P1 through P4. The first patient, P1, has a query button displayed in column C4, which could be activated by a user to initiate a query to determine if the IMD is available for communication. In other embodiments, the IMD can continuously or intermittently transmit its availability. In such embodiments, the proximate monitor will receive the transmission when the IMD is within the transmission range of the proximate monitor and the user interface would display the availability of the IMD in real time without an active query by the user.

Continuing with the embodiment shown in FIG. 3, the system is in the process of searching for the second patient, P2, as indicated in column C4. If desired, a status graphic could also be provided, as shown in column C5, to indicate to the user that the system is searching. For example, the graphic could be a colored (e.g., yellow) dot. The availability of the third patient, P3, shows that the IMD is available for communication. Column C4 in this example indicates the IMD has been found, and column C5 can be provided to represent this information by a colored (e.g., green) dot. The user looked for the IMD associated with the fourth patient, P4, but it was unavailable for communication. In this example, column C4 presents the query button to allow the user to query the IMD again and column C5 shows a colored (e.g., red) dot to quickly convey to the user at a glance that this IMD is unavailable for communication. In some embodiments, a time out feature would be provided to remove the dot in column C5 after a specified period of time (e.g., 30 seconds). After such a time out, the availability indicator portion of the user interface for patient P4 would be the same as for patient P1, in this example.

Figure 4:
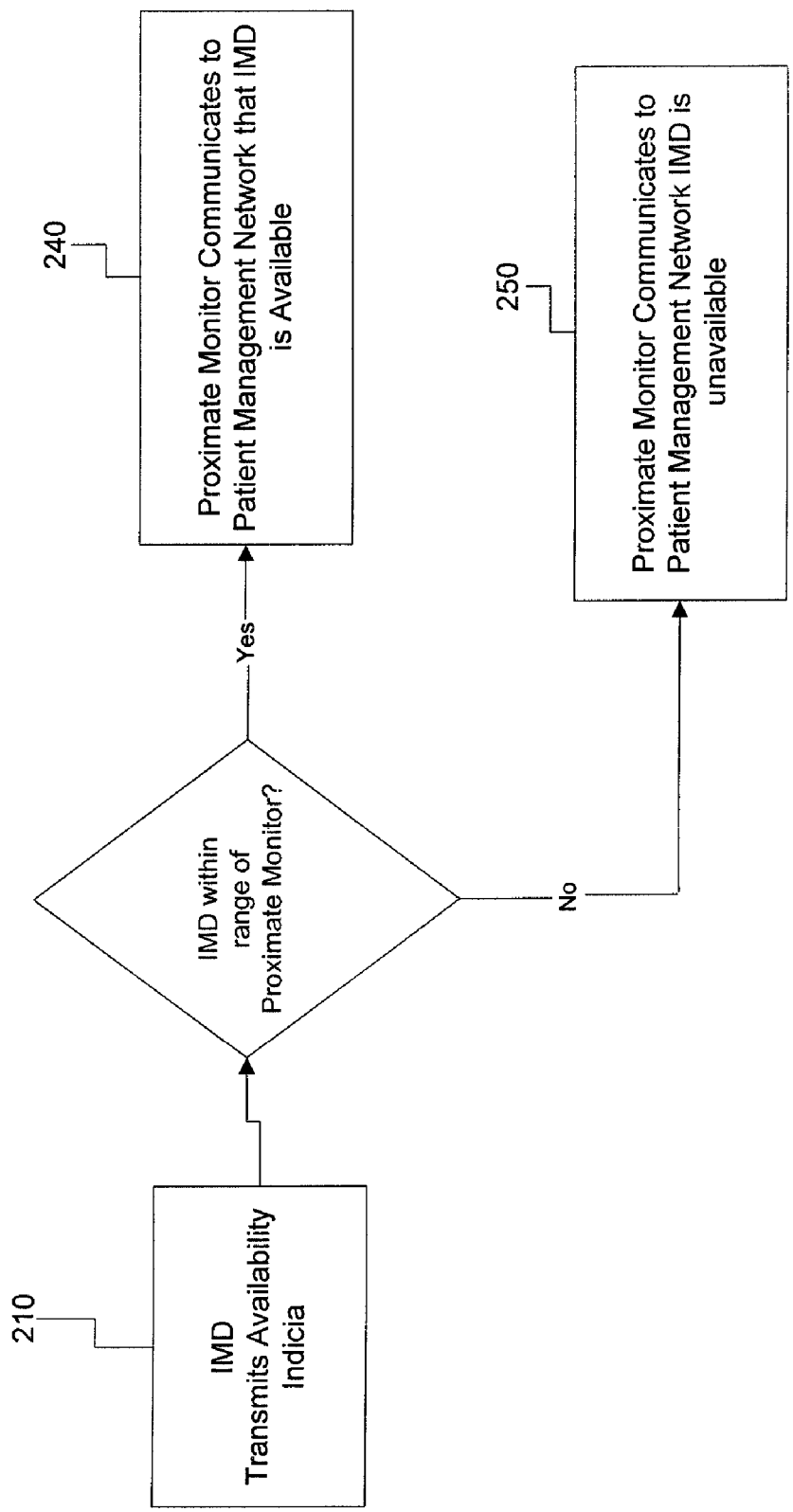
FIG. 4 shows a schematic flow diagram in accordance with an embodiment of the invention.

FIG. 4 shows a flow chart of an embodiment of a communication path between an IMD and a proximate monitor. In the embodiment of FIG. 4, the IMD transmits availability indicia (210). For example, such indicia could include an identifier such as device model number, serial number, hardware, firmware, or software identification, patient name, patient contact information, clinician name, clinician entity and combinations thereof. The transmission of these indicia can occur at any desirable interval. For example, IMD can transmit these indicia hourly or more frequently during the daytime.

As shown in FIG. 4, if the IMD is within range of the proximate monitor, the proximate monitor can communicate to the patient management network that the IMD is available for communication (240). If the IMD is not within range of the proximate monitor, the proximate monitor can communicate to the patient management network that it is not in communication with the IMD (or the patient management network can take the absence of a communication from the proximate monitor that IMD is unavailable) (250). The patient management network can communicate the availability status of the IMD to a clinician in any desirable manner, such as via a web based interface.

Figure 5:
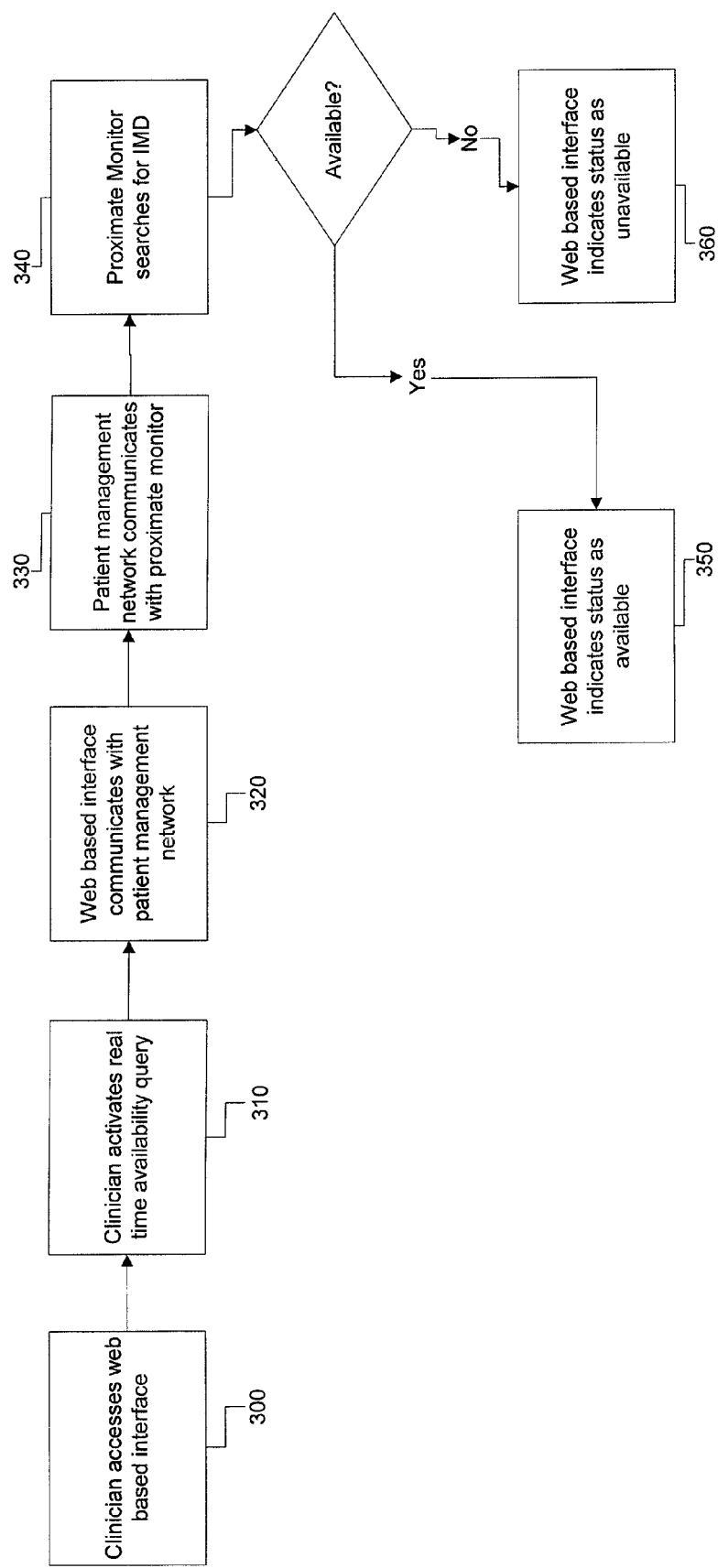
FIG. 5 shows a schematic flow diagram in accordance with an embodiment of the invention.

FIG. 5 shows a flow chart of another embodiment of a communication path between an IMD and a proximate monitor. In the embodiment of FIG. 5, a clinician can access a web based interface (300) and activate a real time availability query for one or more IMDs (310). The query can be transmitted to a proximate monitor (330) through, for example, a patient management network (320). Upon receipt of the query, the proximate monitor can search for the IMD (340). The web based interface can then display the IMDs status as available (350) or unavailable (360), as appropriate.

Embodiments of the availability indicator as described above may be useful for managing data. For example, many IMDs are adapted to upload information such as trends and/or events to patient management networks so clinicians can analyze the data, as discussed above. Generally, after such an upload the IMD itself no longer stores the transmitted information to free storage space. Embodiments of the system as described herein would allow a clinician to determine if an IMD was available for interrogation without having to actually interrogate the device and initiate the IMD to upload this information to the clinicians system.

Further, some clinicians are likely to have many patients with IMDs. Such clinicians may need to periodically interrogate the IMDs. The system as described herein would allow the clinician to quickly determine which IMDs were available for communication without having to attempt to send the communication to determine if the IMD was available, thereby saving time. In addition, in some situations there may be a communication, such as a programming upgrade, that needs to reach many IMDs. The system as described herein would also save the clinician time by allowing the clinician to quickly determine which IMDs were available for communication without having to attempt to send the communication itself.

Embodiments of the availability indicator as discussed above could also be used to verify that a patient has set up their proximate monitor correctly and/or to detect if they are within range of a proximate monitor. Some patients might be concerned about where to place their proximate monitor in their home to ensure successful data transmission. The clinician can perform this test after proximate monitor placement and provide feedback to the patient about the location. An indication that the IMD was available for interrogation would imply the system was set up correctly and would likely properly transmit for data transfers, programming, and emergencies.

Embodiments of the availability indicator as described above may also be useful for testing the communication link from the IMD to patient management network. For example, some IMDs have a feature that sends automated alerts to the patient management network. Testing this communication link offers peace of mind to the clinician and patient that, in the event of an alert, the information will be successfully transferred to the patient management network.

Embodiments of the availability indicator as discussed above would also be useful in many situations outside the home. For example, the availability indicator could be used in a heart failure clinic to identify patients in the waiting room. In such an embodiment, a proximate monitor could be placed within the waiting room to transmit availability queries to and from IMDs. If the availability indicator showed that a patient was present, clinic personnel could then perform programming or interrogations as needed knowing that the patient was in the clinic.

Thus, embodiments of the REMOTE COMMUNICATION SYSTEM WITH AVAILABILITY INDICATOR FOR AN IMPLANTABLE MEDICAL DEVICE are disclosed. One skilled in the art will appreciate that the invention can be practiced with embodiments other than those disclosed. The disclosed embodiments are presented for purposes of illustration and not limitation, and the invention is limited only by the claims that follow.

The invention claimed is:

1. A system comprising, an implantable medical device configured to communicate with a proximate monitor, the proximate monitor configured to communicate with a patient management network accessible by a clinician, the implantable medical device adapted to transmit to the proximate network, and the patient management network visually indicating by a colored status graphic the availability of the medical device in response to receipt of a transmission by the proximate network, wherein the implantable medical device is programmed to continuously transmit its availability to the proximate monitor during operation of the implantable medical device.

2. The system of claim 1, wherein the proximate monitor and the patient management network include a coordinated operation to indicate to the clinician the unavailability of the medical device to communicate.

3. The system of claim 1, wherein the implantable medical device indicates the availability of the medical device to communicate via a web based interface in communication with the patient management network.

4. The system of claim 3, wherein the web based interface indicates availability status via colored dots.

5. The system of claim 3, wherein the web based interface identifies a patient by name.

6. The system of claim 3, wherein the web based interface identifies the medical device.

7. The system of claim 3, wherein the web based interface indicates the last time the medical device communicated.

8. The system of claim 1, wherein the medical device transmits its availability to the proximate monitor by transmitting at least one of device model number, serial number, hardware, firmware, or software identification, patient name, patient contact information, clinician name, clinician entity and combinations thereof.

9. The system of claim 1, wherein the medical device comprises one or more of a pacemaker, a PCD pacemaker/cardioverter/defibrillator, an oxygen sensing device, a nerve stimulator, a muscle stimulator, a drug pump, or an implantable monitoring device.

10. A system comprising, an implantable medical device adapted to transmit its availability to communicate with a proximate monitor, the proximate monitor in communication with a patient management network, and a web based interface in communication with the patient management network, the web based interface visually indicating the availability of the medical device to communicate in real time by a colored status graphic.

11. The system of claim 10, wherein the medical device continuously transmits its availability to the proximate monitor during operation of the medical device.

12. The system of claim 10, wherein the web based interface is adapted to identify one or more of a patient's name or patient identification number.

13. The system of claim 10, wherein the web based interface identifies the medical device and indicates the last time the medical device communicated.

14. The system of claim 10, wherein the medical device comprises one or more of a pacemaker, a PCD pacemaker/cardioverter/defibrillator, an oxygen sensing device, a nerve stimulator, a muscle stimulator, a drug pump, or an implantable monitoring device.

15. The system of claim 10, wherein the transmission by the implantable medical device to the proximate monitor of its availability is performed continuously during operation of the implantable medical device.

16. The system of claim 10, wherein the transmission by the implantable medical device to the proximate monitor of its availability is performed intermittently during operation of the implantable medical device.

17. A system comprising, an implantable medical device, a proximate monitor, a patient management network, and a web based interface, during operation of the system, the implantable medical device transmitting its availability to the proximate monitor when in range of the proximate monitor, the proximate monitor in communication with the patient management network, in response to receipt of a transmission from the proximate monitor the web based interface communicating the availability of the implantable medical device to the patient management network to visually indicate to a user by a colored status graphic whether the implantable medical device is in the range of the proximate monitor, wherein the implantable medical device continuously transmits its availability to the proximate monitor during operation of the implantable medical device.

18. The system of claim 17, wherein the web based interface indicates whether the implantable medical device is able to communicate with the proximate monitor.

19. The system of claim 17, wherein the web based interface indicates the unavailability of the implantable medical device to communicate with the proximate monitor.

20. The system of claim 17, wherein the medical device transmits its availability to the proximate monitor by transmitting at least one of device model number, serial number, hardware, firmware, or software identification, patient name, patient contact information, clinician name, clinician entity and combinations thereof.

21. A system comprising:
an implantable medical device (IMD);
a proximate monitor communicatively coupled to the implantable medical device, wherein the IMD automatically transmits to the proximate monitor a signal indicative of the availability of the IMD; and
a patient management network communicatively coupled to the proximate monitor, wherein the proximate monitor relays the signal received from the IMD to the patient management network and in response to receipt of the signal, the patient management network displays a visual indicator of the availability of the IMD, wherein the transmission by the IMD of the signal is performed continuously during operation of the IMD.

22. The system of claim 21, further comprising a web based interface communicatively coupled with the proximate monitor and the patient management network, wherein the signal relayed from the proximate monitor is transmitted via the web based interface to the patient management network.

* * * * *